(12) United States Patent
Brown

(10) Patent No.: US 7,300,400 B2
(45) Date of Patent: Nov. 27, 2007

(54) PEDIATRIC LIVER RETRACTOR

(75) Inventor: Jerry Milford Brown, Sewaren, NJ (US)

(73) Assignee: Automated Medical Products Corporation, Sewaren, NJ (US)

( * ) Notice: Subject to any disclaimer, the term of this patent is extended or adjusted under 35 U.S.C. 154(b) by 0 days.

(21) Appl. No.: 11/166,171

(22) Filed: Jun. 27, 2005

(65) Prior Publication Data

US 2006/0293566 A1    Dec. 28, 2006

(51) Int. Cl.
*A61B 1/32* (2006.01)
(52) U.S. Cl. .................................... 600/210
(58) Field of Classification Search .............. 600/204, 600/209–211, 217, 235
See application file for complete search history.

(56) References Cited

U.S. PATENT DOCUMENTS

| | | | | |
|---|---|---|---|---|
| 4,143,652 A | | 3/1979 | Meier et al. ............... 128/20 |
| 4,380,999 A | | 4/1983 | Healy ....................... 128/20 |
| 4,610,243 A | * | 9/1986 | Ray ........................ 600/206 |
| 4,616,633 A | * | 10/1986 | Vargas Garcia ........... 600/206 |
| 5,152,279 A | | 10/1992 | Wilk ........................ 128/17 |
| 5,280,782 A | | 1/1994 | Wilk ........................ 128/20 |
| 5,439,476 A | | 8/1995 | Frantzides ............... 606/192 |
| 5,514,077 A | * | 5/1996 | Rabban .................. 600/226 |
| 5,743,853 A | * | 4/1998 | Lauderdale .............. 600/210 |
| 5,941,819 A | * | 8/1999 | Chin ....................... 600/204 |
| 5,964,697 A | * | 10/1999 | Fowler, Jr. ................ 600/210 |
| 5,967,971 A | * | 10/1999 | Bolser ..................... 600/211 |
| 6,228,025 B1 | * | 5/2001 | Hipps et al. .............. 600/213 |
| 6,241,658 B1 | * | 6/2001 | Goodrich ................. 600/210 |
| 6,248,062 B1 | | 6/2001 | Adler et al. .............. 600/204 |
| 6,296,609 B1 | * | 10/2001 | Brau ....................... 600/210 |
| 6,322,499 B1 | * | 11/2001 | Evans et al. .............. 600/212 |
| 6,350,236 B1 | * | 2/2002 | Hipps et al. .............. 600/213 |
| 6,416,465 B2 | * | 7/2002 | Brau ....................... 600/210 |
| 6,468,206 B1 | * | 10/2002 | Hipps et al. .............. 600/213 |
| 6,482,153 B1 | * | 11/2002 | Hipps et al. .............. 600/213 |
| 6,602,188 B2 | * | 8/2003 | Bolser ..................... 600/210 |
| 6,875,173 B2 | * | 4/2005 | Suddaby .................. 600/210 |
| 6,997,872 B1 | * | 2/2006 | Bohanan et al. .......... 600/210 |
| 2002/0013514 A1 | * | 1/2002 | Brau ....................... 600/213 |
| 2002/0111536 A1 | * | 8/2002 | Cuschieri et al. ......... 600/210 |

OTHER PUBLICATIONS

Engineering drawings of Nathanson Hook Liver Retractors, Drawing Nos. 4-981121/1, 4-981121/2, and 4-981121/3 (3 Figures) Sep. 19, 2000.
Engineering drawings of Dbaly's Hook Liver Retractors, Drawing No. 4-981124/1 and 4-981124/2 (2 Figures) Sep. 11, 2000.

\* cited by examiner

*Primary Examiner*—Cary E. O'Connor
(74) *Attorney, Agent, or Firm*—Winston & Strawn LLP

(57) ABSTRACT

A pediatric liver retractor with a supporting shaft configured traversing a pediatric abdominal wall. A hook portion terminating in an insertion tip is configured generally in a U-shape, with a hook aperture and a hook depth, which along with the insertion tip, are configured and dimensioned for supporting and retracting a pediatric liver without damaging the liver to provide access to a surgical site.

24 Claims, 6 Drawing Sheets

PEDIATRIC LIVER RETRACTOR

FIELD OF THE INVENTION

The present invention relates generally to a surgical tool for use during surgical procedures. More particularly, the invention relates to a liver retractor for pediatric surgical procedures.

BACKGROUND OF THE INVENTION

Physicians manipulate liver retractors within the abdominal cavity of patients so that the retractor lifts and retracts the liver, which is a relatively large organ, away from other smaller organs and connective tissue within the cavity to position the liver out of the way of the surgical site where the surgical procedure is to be performed. With the liver positioned in this manner, physicians have a more clear view of the surgical site within the abdominal cavity and have a larger area therein for manipulating other surgical tools during the surgical procedure.

Some known liver retractors are made of a shaft or rod of surgical grade stainless steel that is bent or otherwise formed to obtain a hook-like structure. The structure typically includes a hook portion which holds the liver in place during retraction and a support portion that allows the retractor to be held outside the patient. One type of liver retractor is a Nathanson hook which is used, for example, to retract a liver during bariatric surgical procedures. Nathanson hooks are typically manufactured in standard sizes, the smallest of which includes a hook portion that has a width and a depth each of about 60 mm. Additionally, the hook portion usually includes a bent tip extending from one end thereof that has a length of about 15 mm.

The structural dimensions and configurations of typical Nathanson hooks are selected for use for surgical procedures on adult patients. Nathanson hooks, however, are not used during surgical procedures performed in the abdominal cavity of pediatric patients due to the significantly different physiologies of children. Compared to an adult, and especially an obese adult, the abdominal cavity of a child is substantially smaller, as are the organs and connective tissue contained therein. Additionally, the spacing of the organs is more compact within the abdominal cavity of a child, and there is less room for physicians to manipulate surgical tools therein while performing the surgery. Children's organs are also shaped differently than those of adults, and due to their relatively small abdominal cavities, their organs are also arranged differently as well.

Even the smallest standard Nathanson hooks have lengths and associated angles that are generally designed and configured for use during surgical procedures on adults. While such hooks are suited for safely inserting into an adult to retract an adult liver, there is a need for a liver retractor with a configuration better suited for safe use in pediatric procedures to prevent puncturing the liver or surrounding organs of a child.

In place of Nathanson hooks that are used on adults, physicians typically use a fan-shaped retractor or other similar tool, which is designed to spread or open up into two or three pieces to achieve retraction during pediatric surgeries. The use of these tools, however, provides substantially less control of the liver in the retracted position and also presents a greater risk of damage to the liver and other adjacent organs while positioning the device or while the device holds the liver in the retracted position.

Thus, there is a need for a liver retractor that is configured and dimensioned for use during pediatric surgeries, while reducing the risk of damage to the liver when positioning or holding the liver in the retracted position.

SUMMARY OF THE INVENTION

The present invention relates to a liver retractor for pediatric surgical procedures and a method of making the retractor. The preferred embodiment of the pediatric liver retractor includes a supporting shaft configured for placement traversing a pediatric abdominal wall. The retractor also includes a hook portion configured in a substantially U-shape that defines a hook aperture and a hook depth configured and dimensioned for supporting and retracting a pediatric liver while minimizing and avoiding liver damage to provide access to a surgical site. The hook portion extends from the supporting portion on a first side of the U-shape. An insertion tip extends from a second side of the U-shape at a tip angle and with a tip length selected to facilitate insertion of the tip into a laparoscopic incision and rotation during insertion of the hook within the incision to a retracted position in which the tip at least partly faces an internal side of the abdominal wall. At least the hook portion can support and at least partly retract the liver, while substantially minimizing or avoiding the likelihood of damaging internal organs during insertion and rotation to the retracted position in a pediatric patient.

Preferably, the length of the insertion tip is about 5 mm to 13 mm. Additionally, the tip angle is preferably selected such that the insertion tip is angled downwardly away from the liver when the hook portion is in the retracted position. More preferably, the first side of the U-shape extends generally along a first plane, and the tip angle is selected such that the insertion tip is angled downwardly with respect to the first plane by a downward tip angle of about 10° to 30° and even more preferably with a tip length of about 8 to 17 mm. The tip angle is also preferably selected such that the insertion tip is angled away from the first side of the U-shape at an open tip angle. More preferably, the open tip angle is about 25° to 45°.

The pediatric liver retractor also preferably has a hook depth of about 30 mm to 60 mm and a hook aperture that has a width of about 25 mm to 55 mm. More preferably, the hook portion has a ratio of hook depth to hook aperture of about 1 to 1.25.

The first side of the U-shape extends generally along a first plane, and the second side is preferably oriented at a second angle with respect to the first plane, such that the second side is angled towards the liver in the retracted position. More preferably, the second angle is about 8° to 13°. The pediatric liver retractor also preferably includes a mount portion extending upwardly in the retracted position from the supporting shaft to mount to a tool holder to support the liver in the retracted position.

In the preferred embodiment, the pediatric liver retractor preferably includes a first leg extending from the supporting shaft, a second leg from which the tip insertion tip extends, and an intermediate portion connecting the first and second legs at first and second ends thereof, respectively, so that the first and second legs define a hook angle of about 6° to 20°. Preferably, the intermediate portion is substantially arcuate and the first and second legs are substantially straight. More preferably, the arcuate intermediate portion has a radius of about 10 mm to 20 mm.

Preferably, the first leg and first end of the intermediate portion are disposed on a first plane, the second leg is oriented at a second angle with respect to the first plane, and the insertion tip is oriented at a downward tip angle with respect to the first plane and at a open tip angle away from the first leg, such that the second leg is angled upwardly towards the liver in the retracted position, and the insertion tip is angled downwardly away from the liver in the retracted position. More preferably, the second angle is from about 8° to 13°, the downward tip angle is from about 10° to 30°, and the open tip angle is from about 25° to 45°. Additionally, the supporting shaft preferably has a centerline, and first leg extends from the supporting shaft at a first angle from the supporting shaft centerline measured along the first plane of about 0° to 45°.

The invention thus provides a liver retractor that is configured and dimensioned for manipulation and positioning within the abdominal cavity of a pediatric patient such that the retractor can support and maintain the liver in a retracted position.

DETAILED DESCRIPTION OF THE PREFERRED EMBODIMENTS

Figure 1:
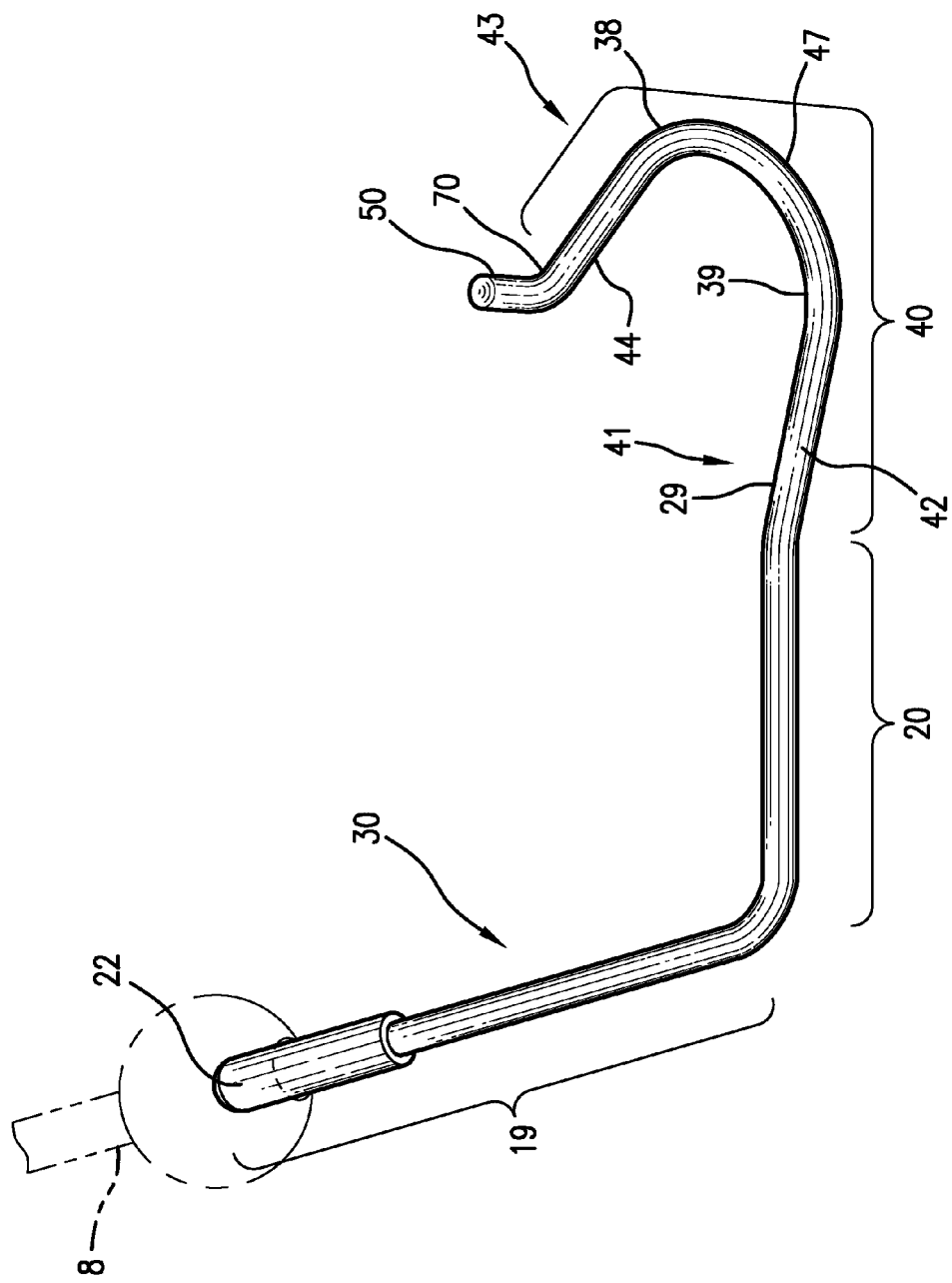
FIG. 1 is a perspective view of a first preferred embodiment of the liver retractor, constructed according to the present invention.
Figure 3:
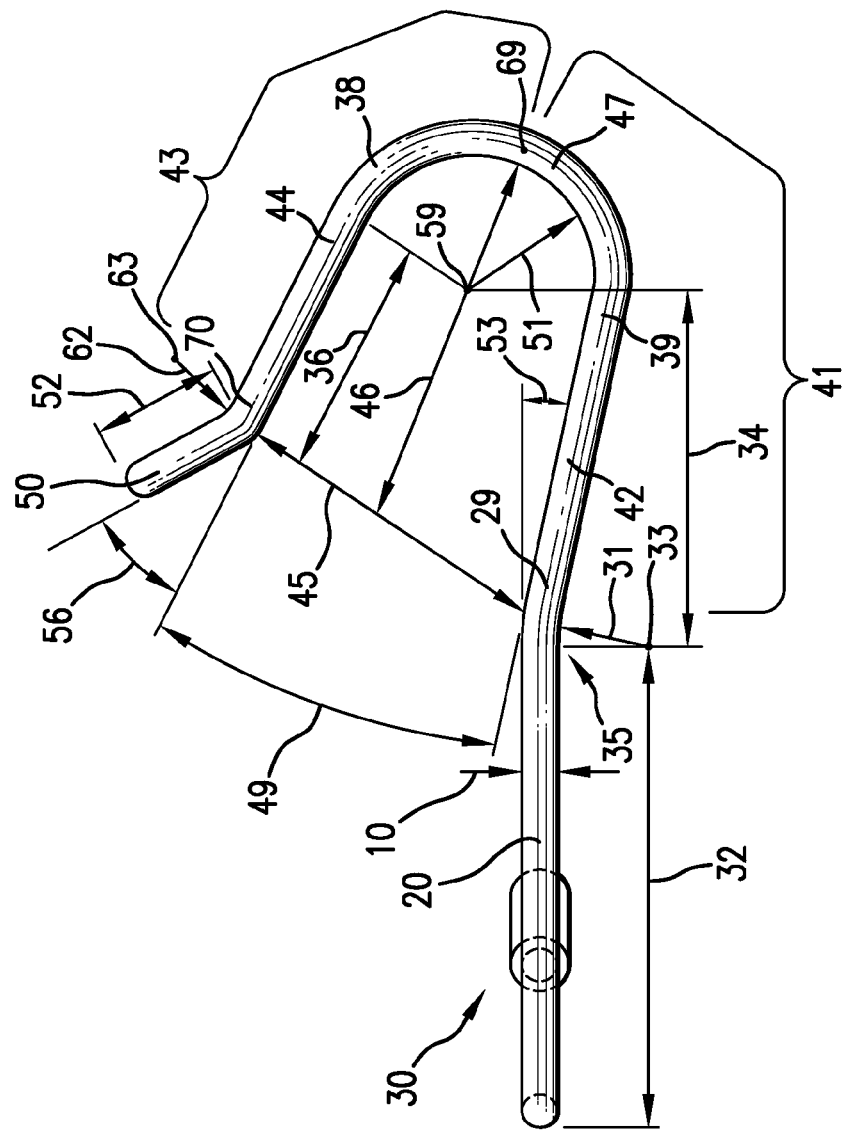
FIG. 3 is a bottom view thereof.
Figure 4:
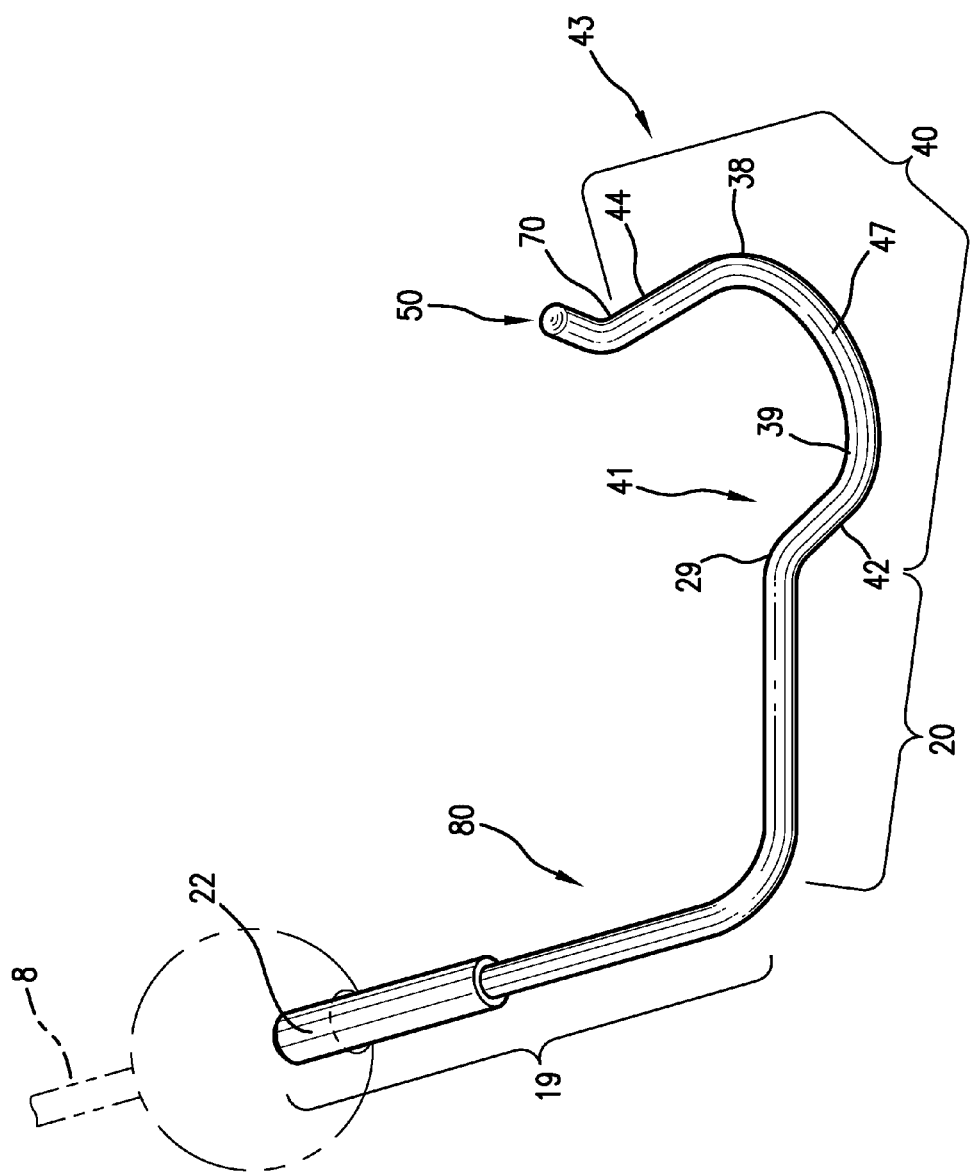
FIG. 4 is a perspective view of a second preferred embodiment of the liver retractor, constructed according to the present invention.
Figure 6:
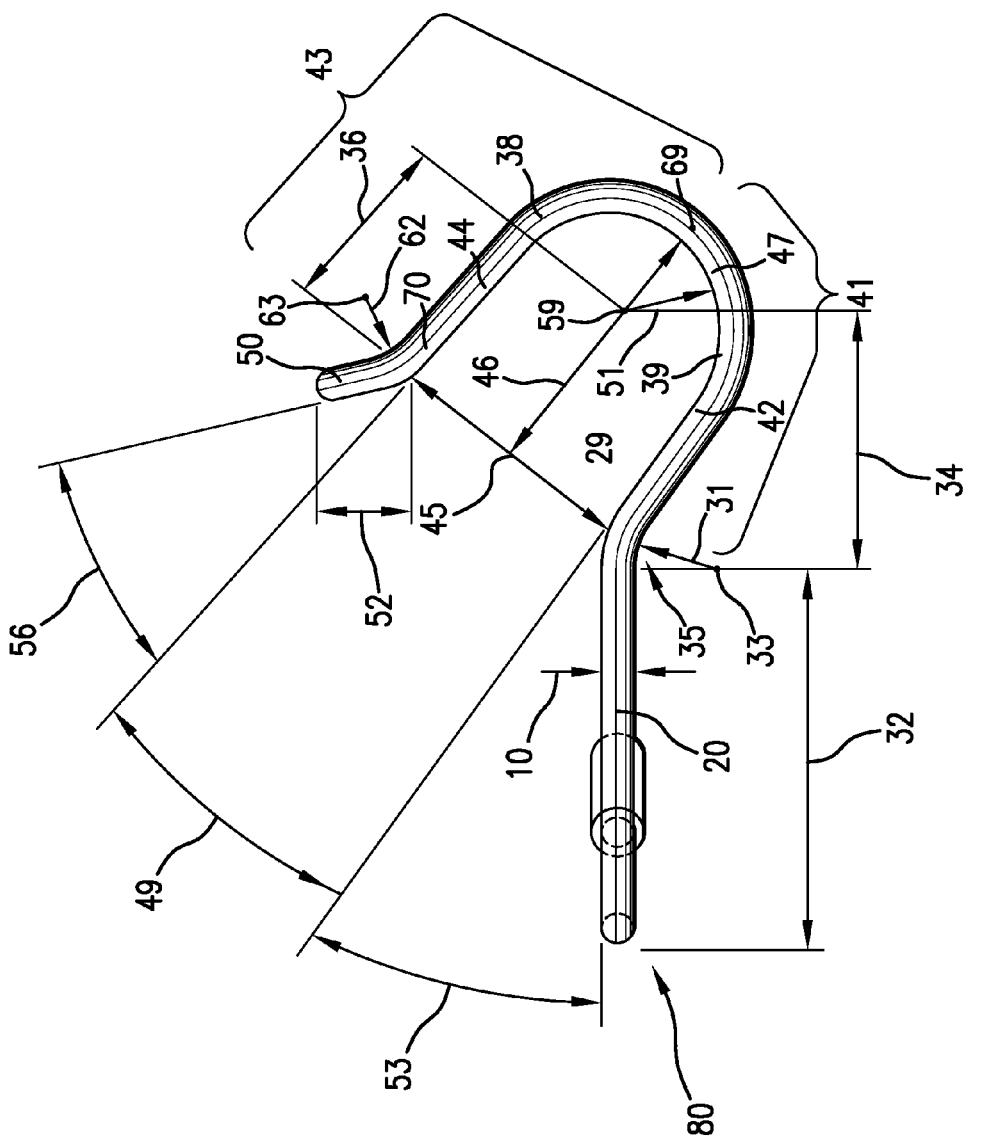
FIG. 6 is a bottom view thereof.

FIGS. 1 and 4 show, respectively, a first preferred embodiment 30 and a second preferred embodiment 80 of the pediatric liver retractor that include a mount portion 19, a supporting shaft 20, a hook portion 40, and an insertion tip 50. Preferably, the liver retractor 30,80 is made of a unitary material, such as of surgical grade stainless steel, and includes a shaft or rod that is bent or otherwise formed in the desired shape. Alternatively, the retractor 30,80 can be made of separate pieces that have preferably been integrally joined. More preferably, the bent shaft or rod forming the main body of the liver retractor 30, 80 has a diameter 10, as shown in FIGS. 3 and 6, of less than about 6 mm and even more preferably of less than about 5 mm and at least about 2 mm.

The term "pediatric patient," as used herein, should generally be understood to refer to a patient under the age of 16. One embodiment of the liver retractor is preferably intended for use during surgical procedures on older pediatric patients, preferably of ages from about 12 to 16. Another embodiment of the liver retractor is preferably intended for use on younger pediatric patients of ages from about 6 to 10, and yet another embodiment of the liver retractor is intended for use on pediatric patients of ages from about 2 to 6. Still yet another embodiment is preferably intended for use on pediatric patients younger than about the age of 2. It should be understood that references to downward, upward, horizontal, and vertical directions, as used herein, are made with respect to a patient's liver with the retractor in the retracted position, with the upward direction being generally toward the patient's head and the downward direction being generally toward the patient's feet.

The mount portion 19 preferably includes an enlarged gripping member 22 that is configured and dimensioned for associating with a surgical tool support 8, as shown in FIGS. 1 and 4, which can be further fixedly attached to the operating room table, for example, as known in the art. Preferably, the gripping member 22 is configured for secured holding by a surgical tool support, such as described in U.S. Pat. No. 4,143,652, or a surgical tool support of the system sold under the tradename Iron Intern® by Automated Medical Products Corp. Preferably, the mount portion 19 has a length 21 of less than about 120 mm and even more preferably of less than about 100 mm and at least about 40 mm. In the first preferred embodiment 30, the mount portion 19 has a length of about 95 mm, and in the second preferred embodiment 80, the mount portion 19 has a length of about 60 mm. It should be noted that the lengths of the portions of the liver retractor, as referenced herein, are measured along their respective axes in the preferred embodiments 30, 80. The gripping member 22 preferably has a length 23 from about 30 to 50 mm and more preferably of about 40 mm, and a diameter 25 from about 6 to 10 mm and more preferably of about 8 mm. In the preferred embodiments 30, 80, the mount portion 19 is substantially straight, and the gripping member 22 is a cap or fitting with an cylindrical configuration that is fixed over the free end of the mount portion 19, such as by welding or adhering. In other embodiments, the gripping member 22 has another configuration that allows it to be gripped by a surgical tool support.

Referring to FIGS. 1, 2, 4, and 5, the supporting shaft 20 is preferably configured for placement traversing the abdominal wall of a pediatric patient. The supporting shaft 20 also preferably extends from the end of the mount portion 19 that is opposite the gripping member 22, preferably at an angle 24. The angle 24 is preferably selected such that upon insertion of the hook portion 40 within the abdominal cavity of a pediatric patient and positioning thereof in the retracted position with supporting shaft 20 traversing the patient's abdominal wall, the mount portion 19 extends upwardly, although preferably at an angle to the vertical, from the supporting shaft 20 and is oriented such that the gripping member 22 can be gripped by a surgical tool support. Advantageously, this allows the surgical tool support to stably support and maintain the liver retractor 30, 80 in the retracted position throughout the duration of the surgical procedure. Preferably, the angle 24 is from about 50° to 100° and more preferably is from about 70° to 80°. In the first and second preferred embodiments 30, 80, the angle 24 is 75°. In other embodiments, supporting shaft 20 is substantially orthogonal to the mount portion 19.

As shown in FIGS. 1, 3, 4, and 6, the hook portion 40 preferably includes a first side 41 and a second side 43. Preferably, the first side 41 includes a first leg 42 that is connected at one end 29 to the supporting shaft 20 at an angle 53. The first side 41 also includes part of an intermediate portion 47 that is connected to the other end 39 of the first leg 42. The second side 43 preferably includes a second leg 44 that is connected at one end 70 to the insertion tip 50. The second side also includes part of the intermediate portion 47 that is connected to the other end 38 of the second leg 44. Thus, the first side 41 preferably includes the first leg 42 and part of the intermediate portion 47, from the end 29 of the first leg 42 to the bottom 69 of the intermediate portion 47, and the second side 43 preferably includes the second leg 44 and part of the intermediate portion 47, from the end 70 of the second leg 44 to the bottom 69 of the intermediate portion 47.

Preferably, the intermediate portion 47 is curved, more preferably in a smooth arc, although a segmented or varying curve can alternatively be used. The first and second legs 42, 44 extend from the intermediate portion 47 with respect to each other at an angle 49, projected on a plane as shown in FIGS. 3 and 6. Preferably, the angle 49 is less than about 30° and greater than 3°, which advantageously maintains the legs 42, 44 in a desirable configuration for evenly and stably supporting thereon the weight and girth of a liver of a pediatric patient. More preferably, the angle 49 is from about 6° to 20°. In the first preferred embodiment 30, the first and second legs 42, 44 are substantially straight and extend from the intermediate portion 47 at an angle 49 of about 17°. In the second preferred embodiment 80, the first and second legs 42, 44 extend at an angle 49 of about 8°.

In the preferred embodiments 30, 80, the arcuate shape of the intermediate portion 47 also preferably has a substantially constant radius 51, which is defined from the center of curvature 59 of the intermediate portion 47 located within the space enclosed by the hook portion 40. Preferably, the radius 51 is less than about 30 mm and more preferably is less than about 20 mm and greater than about 5 mm. Even more preferably, the radius 51 is from about 10 mm to 20 mm. In the first preferred embodiment 30, the intermediate portion 47 has a radius 51 of about 17 to 18 mm, and in the second preferred embodiment 80, the intermediate portion 47 has a radius 51 of about 13 mm. In an alternative embodiment, the intermediate portion 47 can have a varying radius.

Figure 2:
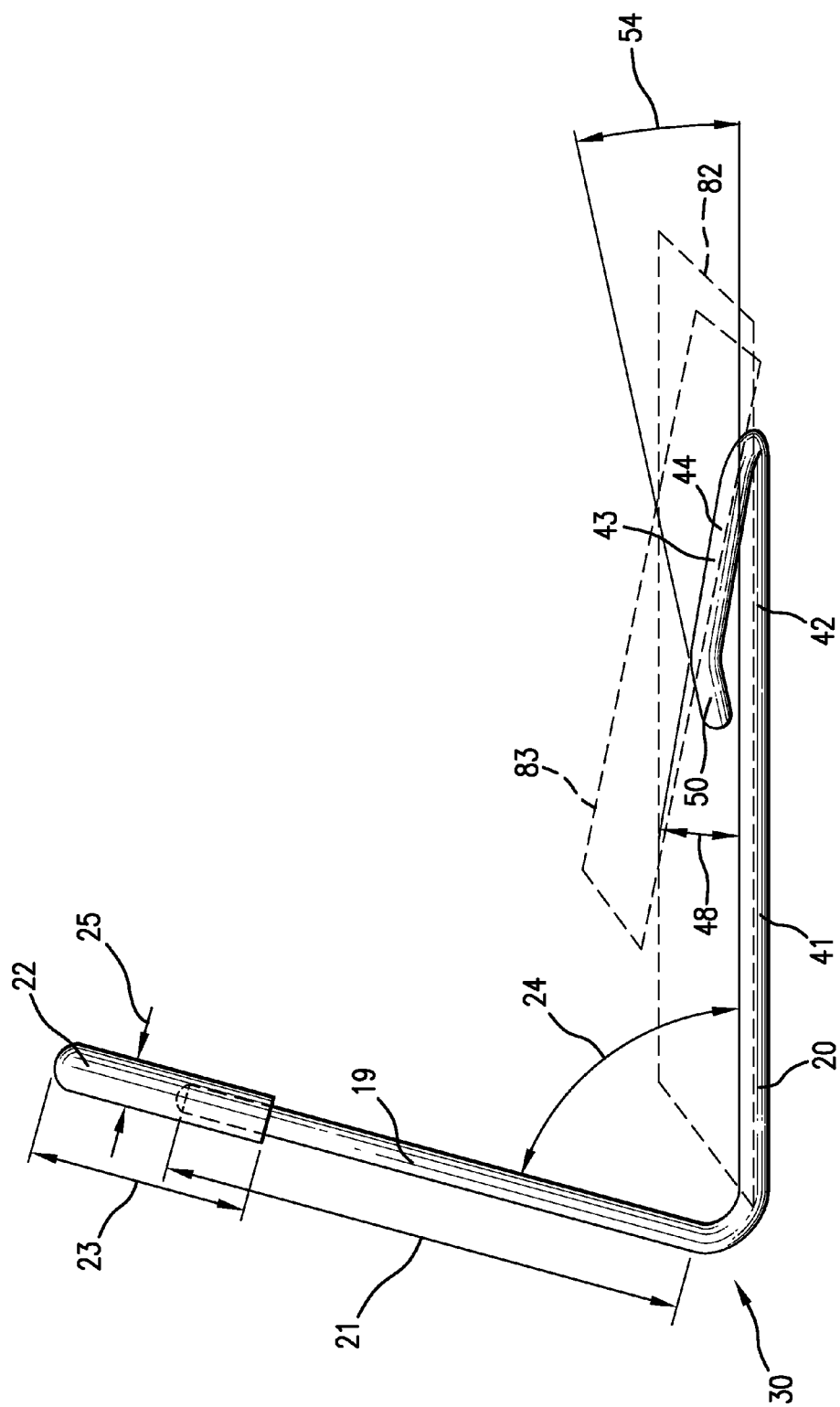
FIG. 2 is a side view thereof.
Figure 5:
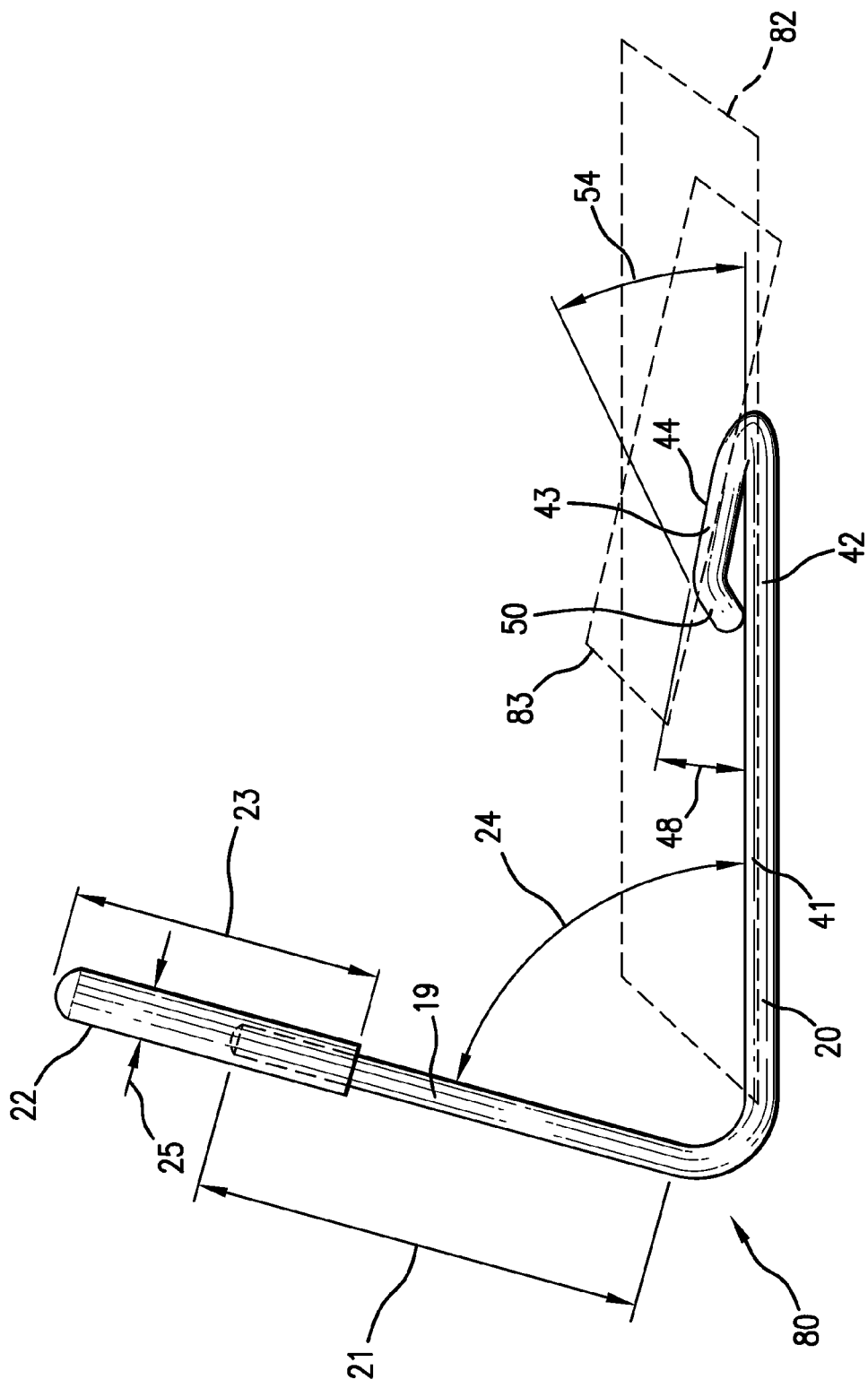
FIG. 5 is a side view thereof.

Preferably, the first leg 42 and first side 41 of the hook portion 40 extend from the supporting shaft 20 at an angle 53 from the centerline of the supporting shaft 20 measured along a first plane 82 shown in FIGS. 2 and 5. The angle 53 is preferably less than 60° and more preferably is less than 50° and greater than 5°. Even more preferably, the angle 53 is from about 40° to 10°. In the first preferred embodiment 30, the angle 53 is about 39°, and in the second preferred embodiment 80, the angle 53 is about 12°. The connection between the supporting shaft 20 and the first leg 42 also defines a bend 35 that has a radius 31 defined from the center of curvature 33. Preferably, the radius 31 is less than about 20 mm and more preferably is less than about 15 mm and greater than about 5 mm. In the second preferred embodiment 80, the radius 31 is from about 12 mm to 13 mm.

The length 32 of the supporting shaft 20, which is shown in FIGS. 3 and 6 and, in the preferred embodiment, is measured between the end thereof that connects to the first leg 42 and the end that connects to the mount portion 19, preferably is sufficient such that the supporting shaft 20 can traverse the abdominal wall of a pediatric patient when the retractor 30, 80 is in the retracted position. Preferably, the length 32 is less than about 80 mm and more preferably is less than about 70 mm and greater than about 30 mm. Even more preferably, the length 32 is from about 60 mm to 40 mm. In the first preferred embodiment 30, the length 32 of the supporting shaft 20 is about 60 mm, and in the second preferred embodiment 80, the length 32 is about 45 mm.

The length 34 of the first leg 42, which is also shown in FIGS. 3 and 6 and, in the preferred embodiment, is measured between the end thereof that connects to the supporting shaft 20 and the end that is tangential with the center of curvature 59 of the intermediate portion 47, preferably is less than about 70 mm and more preferably is less than about 60 mm and greater than about 20 mm. Even more preferably, the length 34 is from about 25 mm to 55 mm. In the first preferred embodiment, the length 34 of the lower portion 61 is about 50 mm, and in the second preferred embodiment, the length 34 is about 30 mm.

The second leg 44 of the second side 43 of the hook portion 40 preferably has a length 36 that, along with the first leg 42, is sufficient to safely support and retract the liver and also reduce the risk of damage to internal organs or the abdominal wall during insertion and rotation of the hook portion 40. Preferably, the length 36 of the second leg 44, which in the preferred embodiment is measured between the end thereof that is tangential to the center of curvature 59 of the intermediate portion 47 and the end that connects to the insertion tip 50, is less than about 50 mm and more preferably is less than about 40 mm and greater than about 15 mm. Even more preferably, the length 36 is from about 35 mm to 20 mm. In the first preferred embodiment 30, the length 36 is about 35 mm, and in the second another preferred embodiment 80, the length 36 is about 20 mm.

Preferably, the first leg 42 is longer than the second leg 44. Advantageously, this proportional configuration of the legs 42, 44 of the hook portion 40 better allows the hook portion 40 to conform to and support the shape of a pediatric liver in the retracted position. Preferably, the ratio of length 34 to length 36 is greater than about 1 and more preferably is greater than about 1.33 and less than about 2. In the first preferred embodiment 30, the ratio of lengths is about 1.5, and in the second preferred embodiment 80, the ratio is about 1.66.

The hook portion 40 preferably has a U-shape configuration, which advantageously allows the weight of the liver to be supported substantially evenly along the legs 42, 44 of the hook portion 40 when it is positioned under the liver in the retracted position. The hook portion 40 can alternatively have other shapes and configurations to allow retraction of the liver or other organs within the abdominal cavity of a pediatric patient. The supporting shaft 20 and the hook portion 40 extending therefrom preferably have a J-shape configuration. Additionally, the J-shape of the retractor 30, 80 is preferably oriented with the hook portion 40 open to the right when viewed from the bottom, as shown in FIGS. 3 and 6, to accommodate the natural position of the liver in the right side of the abdominal cavity.

The lengths and curvatures, if any, of the first and second legs 42, 44, the intermediate portion 47, and the angle 49 of the U-shape hook portion 40 define the dimensions and configuration of a hook aperture 45 and a hook depth 46 of the hook portion 40. Preferably, the hook aperture 45 and hook depth 46 are configured for supporting and retracting the pediatric liver to the retracted position, while minimizing or avoiding damage thereto during insertion and retraction, to provide visual clearance and spatial access to a surgical site.

The hook aperture 45 of the U-shape has a width, which is the distance at the opening of the hook portion 40 between the end 29 of the first leg 42 and the end 70 of the second leg 44. The width of the hook aperture 45 is preferably sufficiently narrow such that the hook portion 40 can be manipulated and positioned within the abdominal cavity of a pediatric patient without damaging contact with other organs, while supporting the girth of a pediatric liver on the first and second legs 42, 44 when the hook portion 40 is positioned under the liver. Preferably, the width of the hook aperture 45 is less than about 70 mm and more preferably is less than about 60 mm and greater than about 20 mm. Even more preferably, the width is from about 25 mm to 55 mm. In the first preferred embodiment 30, the width of the hook aperture 45 is about 50 mm, and in the second preferred embodiment 80, the width of the hook aperture 45 is about 30 mm.

The hook depth 46 of the U-shape is defined as the distance from the bottom 69 of the intermediate portion 47 to the center of the boundary of the hook aperture 45. The hook depth 46 is preferably sufficiently short such that the hook portion 40 can be inserted, rotated, and positioned within the abdominal cavity of a pediatric patient without damaging other organs. The hook depth 46 is also sufficiently short such that the insertion tip 50 that extends from the second side 43 does not compress against the abdominal wall during rotation of the retractor 30, 80 to the retracted position. Preferably, the hook depth 46 is less than about 70 mm and more preferably is less than about 65 mm and greater than about 25 mm. Even more preferably, the hook depth 46 is from about 30 mm to 60 mm. In the first preferred embodiment 30, the hook depth 46 is about 55 mm, and in the second preferred embodiment 80, the hook depth 46 is about 35 mm.

As shown in FIGS. 2 and 4, the supporting shaft 20 and the first leg 42 of the U-shape hook portion 40 preferably extend generally along a first plane 82 that is substantially horizontal. More preferably, the entire first side 41 of the hook portion 40 extends along the first plane 82. Preferably, the second leg 44, and more preferably the second side 43, extends along a second plane 83, which is preferably oriented at an angle 48 such that the second side 43 and second leg 44 are angled upwardly towards the liver in the retracted position. Advantageously, angling the second side 43 at such an angle 48 from the first plane 82 substantially reduces or avoids the risk that the insertion tip 50 will catch or snag other internal organs as the retractor 30, 80 is inserted or rotated to the retracted position. Preferably, the angle 48 between the first plane 82 and the second side 43 is less than about 20° and more preferably is less than about 15° and greater than about 5°. Even more preferably, the angle 48 is from about 8° to 13°. In the first preferred embodiment 30, the angle 48 is about 12°, and in the second preferred embodiment 80, the angle 48 is about 10°.

The insertion tip 50 extends from the end 70 of the second side 43 and second leg 44 of the U-shape hook portion 40. Preferably, the free end of the insertion tip 50 is rounded or otherwise blunt, and the insertion tip 50 is dimensioned and configured for penetration through an incision in the abdominal wall of a pediatric patient such that the hook portion 40 can follow therethrough and rotate under the liver before retraction. The insertion tip 50 is preferably configured to penetrate the abdominal wall through a laparoscopic incision. The insertion tip 50 preferably has a length 52 that is long enough to penetrate the abdominal wall to gain entry into the abdominal cavity of a pediatric patient, but short enough such that the risk of puncture or laceration of internal organs or connective tissue therein is significantly reduced, compared to an adult-sized Nathanson hook, upon rotation of the hook portion 40 to the retracted position. The length 52 of the insertion tip 50 is also sufficiently short such that the insertion tip 50 does not compress against the abdominal wall during rotation of the retractor 30, 80 to the retracted position. The length 52 of the insertion tip 50 is preferably less than about 20 mm and greater than about 5 mm. More preferably, the length 52 of the insertion tip 50 is from about 8 mm to 17 mm for older pediatric patients and from about 5 mm to 13 mm for younger pediatric -patients. In the first preferred embodiment 30, the length 52 is about 15 mm, and in the second preferred embodiment 80, the length 52 is about 10 mm.

Preferably, the ratio of the length 52 of the insertion tip 50 to the length 36 of the second leg 44 is such that the insertion tip 50 does not extend far from the end 70 of the second leg 44 to cause a significant risk that the tip 50 may puncture or lacerate other organs upon insertion of the hook portion 40 in the abdominal cavity and rotation under the liver. Preferably, the ratio of the length 52 to length 36 is greater than about 0.4 and less than about 0.66. In the first and second preferred embodiments 30, 80, the ratio of the two lengths is about 0.5.

The insertion tip 50 also preferably extends from the second leg 44 at a downward angle 54 with respect to the first plane 82 and the second leg 44, as shown in FIGS. 2 and 4. Angle 54 is selected so that the insertion tip 50, when rotated to the retracted position, is angled away from the liver and other organs such that the tip does not snag or catch the organs. The angle 54 orients the insertion tip 50 such that it generally faces towards the abdominal wall, which also substantially minimizes or avoids the likelihood that the insertion tip 50 will puncture, lacerate, or otherwise cause damage upon insertion and rotation. Preferably, the downward angle 54 of the insertion tip is greater than about 8° and less than about 40°. More preferably, the angle 54 is from about 10° to 30°. In the first preferred embodiment 30, the downward angle 54 is about 12°, and in the second preferred embodiment 80, the angle 54 is about 28°.

In addition to being oriented at a downward angle 54, the insertion tip is also oriented at an open angle 56 away from the first side 41 of the U-shape hook portion 40, as shown in FIGS. 3 and 6. The open angle 56 also orients the insertion tip 50 away from the liver in the retracted position to reduce the risk of damage to the liver or other organs that may be caused by the retractor 30, 80. Preferably, the open angle 56 is greater than about 20° and less than about 60°. More preferably, the open angle 56 is from about 25° to 45°. In the first preferred embodiment 30, the open angle 56 is about 30°, and in the second preferred embodiment 80, the open angle 56 is about 40°.

Preferably, all bends between portions of the liver retractor 30, 80 are smooth to reduce the risk that the liver and other internal organs may be damaged upon insertion and rotation of the retractor 30,80 within the abdominal cavity. Therefore, a curve of radius 62 is preferably provided at the connection between the insertion tip 50 and the second leg 44. The radius 62 extends from the center of curvature 68 to the connection between the second leg 44 and the insertion tip 50 and is preferably less than about 20 mm and is more preferably less than about 15 mm and greater than about 5 mm. In the first preferred embodiment 30, the radius 62 is about 15 mm, and the second preferred embodiment 80, the radius is about 7 to 8 mm.

As described above, the liver retractor 30, 80 is preferably configured for insertion into the abdominal cavity of a pediatric patient. Insertion of the retractor 30, 80 is achieved by orienting the retractor 30, 80 such that the insertion tip 50 can be inserted through an incision, preferably a laparoscopic incision. Since the insertion tip 50 is angled away from the first side 41 of the U-shape hook portion 40 and at a downward again with respect to the first plane 82, a physician can more easily align the insertion tip 50 with the incision for initial insertion therethrough. Once the insertion tip 50 is inserted, the hook portion 40 and supporting shaft 20 can follow through the incision thereafter until the support shaft 20 traverses the abdominal wall and the hook portion 40 is positioned under the liver. The retractor 30, 80 is then rotated and lifted to the retracted position such that the liver is substantially supported thereon. As the retractor 30, 80 is rotated, the relatively short length 52 of the insertion tip 50 and its configuration pointed back toward the abdominal wall reduces the risk that the insertion tip 50 may catch or snag other organs or surrounding connective tissue. Once in the retracted position, the gripping member 22 of the mount portion 19 can be held or attached to a surgical tool support 8 to securely fix and maintain the retractor 30, 80, and the liver supported thereon, in the retracted position.

Advantageously, the configuration and dimensions of the supporting shaft 20, the hook portion 40, and the insertion tip 50 allow the retractor 30, 80 to be manipulated within the relatively small and crowded abdominal cavity and around the relatively small and compressed internal organs of a pediatric patient to support the liver in the retracted position. Furthermore, the retractor 30, 80 is configured such that the risk of puncture or laceration to organs within the cavity is significantly reduced during manipulation of the retractor 30, 80 to the retracted position. While each of the dimensional and configurational features described above helps reduce or prevent damage to the liver or other internal organs, the combination of such features is preferably selected to achieve a highly safe liver retractor for use during surgical procedures on pediatric patients.

The term "about," as used herein, should generally be understood to refer to both the corresponding number and a range of numbers. Moreover, all numerical ranges herein should be understood to include each tenth of an integer within the range.

While illustrative embodiments of the invention are disclosed herein, it will be appreciated that numerous modifications and other embodiments can be devised by those of ordinary skill in the art. For example, different shapes can be used, such as curved first and second legs or a curved supporting shaft. Features of the embodiments described herein can also be combined, separated, interchanged, and/or rearranged to generate other embodiments. Therefore, it will be understood that the appended claims are intended to cover all such modifications and embodiments that come within the spirit and scope of the present invention.

What is claimed is:

1. A pediatric liver retractor, comprising:
   a supporting shaft configured for placement traversing a pediatric abdominal wall;
   a hook portion configured in a substantially U-shape that defines a hook aperture and a hook depth configured and dimensioned for supporting and retracting a pediatric liver while minimizing or avoiding liver damage to provide access to a surgical site, the hook portion extending from the supporting shaft on a first side of the U-shape; and
   an insertion tip extending from a second side of the U-shape at a tip angle and with a tip length selected to facilitate insertion of the tip into a laparoscopic incision and rotation during insertion of the hook within the incision to a retracted position in which the tip at least partly faces an internal side of the abdominal wall and at least the hook portion can support and at least partly retract the liver, while substantially minimizing or avoiding the likelihood of damaging internal organs during insertion and rotation to the retracted position in a pediatric patient,
   wherein the first side of the U-shape extends generally along a first plane, and the tip angle is selected such that the insertion tip is angled downwardly away from the liver when the hook portion is in the retracted position and, with respect to the first plane, by a downward tip angle of about 10° and 30°.

2. The pediatric liver retractor of claim 1, wherein the tip length is about 8 mm and 17 mm.

3. A pediatric liver retractor, comprising:
   a supporting shaft configured for placement traversing a pediatric abdominal wall;
   a hook portion configured in a substantially U-shape that defines a hook aperture and a hook depth configured and dimensioned for supporting and retracting a pediatric liver while minimizing or avoiding liver damage to provide access to a surgical site, the hook portion extending from the supporting shaft on a first side of the U-shape; and
   an insertion tip extending from a second side of the U-shape at a tip angle and with a tip length selected to facilitate insertion of the tip into a laparoscopic incision and rotation during insertion of the hook within the incision to a retracted position in which the tip at least partly faces an internal side of the abdominal wall and at least the hook portion can support and at least partly retract the liver, while substantially minimizing or avoiding the likelihood of damaging internal organs during insertion and rotation to the retracted position in a pediatric patient,
   wherein the tip angle is selected such that the insertion tip is angled away from the first side of the U-shape at an open tip angle.

4. The pediatric liver retractor of claim 3, wherein the open tip angle is from about 25° to 45°.

5. The pediatric liver retractor of claim 3, wherein the hook depth is from about 30 mm to 60 mm, and the hook aperture has a width of about 25 mm to 55 mm.

6. The pediatric liver retractor of claim 5, wherein the hook portion has a hook depth to hook aperture ration of about 1 and 1.25.

7. The pediatric liver retractor of claim 3, wherein the hook aperture is about 25 mm to 55 mm the hook depth is about 30 mm to 60 mm, the insertion tip extends from a second side of the U-shape at a downward tip angle of about 10° to 30°, and the tip length is about 5 mm to 13 mm.

8. A method of making the pediatric liver retractor of claim 3 which comprises:
   providing an elongated length of surgical-grade material; and
   shaping the elongated length of material to form the supporting shaft the hook portion and the insertion tip.

9. The method of claim 8, wherein the elongated length is a unitary material.

10. The retractor of claim 3, wherein the supporting shaft, hook portion, and insertion tip are associated in smooth configuration to minimize or avoid damage to the pediatric liver and other internal organs upon insertion and rotation of the retractor within the abdominal cavity and upon retracting contact with the liver.

11. The retractor of claim 3, wherein the supporting shaft, hook portion, and insertion tip are made of a unitary rod.

12. The pediatric liver retractor of claim 3, further comprising a mount portion extending upwardly in the retracted position from the supporting shaft to mount to a tool holder to support the liver in the retracted position.

13. The pediatric liver retractor of claim 3, wherein the hook portion comprises:
   a first leg extending from the supporting shaft,
   a second leg from which the tip insertion tip extends, and
   an intermediate portion connecting the first and second legs at first and second ends thereof, respectively, so that the first and second legs define a hook angle of about 6° to 20°.

14. The pediatric liver retractor of claim 3, wherein the tip length is about 5 mm to 13 mm.

15. A pediatric liver retractor, comprising:
a supporting shaft configured for placement traversing a pediatric abdominal wall;
a hook portion configured in a substantially U-shape that defines a hook aperture and a hook depth configured and dimensioned for supporting and retracting a pediatric liver while minimizing or avoiding liver damage to provide access to a surgical site, the hook portion extending from the supporting shaft on a first side of the U-shape; and
an insertion tip extending from a second side of the U-shape at a tip angle and with a tip length selected to facilitate insertion of the tip into a laparoscopic incision and rotation during insertion of the hook within the incision to a retracted position in which the tip at least partly faces an internal side of the abdominal wall and at least the hook portion can support and at least partly retract the liver, while substantially minimizing or avoiding the likelihood of damaging internal organs during insertion and rotation to the retracted position in a pediatric patient,
wherein the first side of the U-shape extends generally along a first plane, and the second side is oriented at a second angle with respect to the first plane, such that the second side is angled towards the liver in the retracted position.

16. The pediatric liver retractor of claim 15, wherein the second angle is from about 8° to 13°.

17. The pediatric liver retractor of claim 15, further comprising a mount portion extending upwardly in the retracted position from the supporting shaft to mount to a tool holder to support the liver in the retracted position.

18. The pediatric liver retractor of claim 15, wherein the hook portion comprises:
a first leg extending from the supporting shaft,
a second leg from which the tip insertion tip extends, and
an intermediate portion connecting the first and second legs at first and second ends thereof, respectively, so that the first and second legs define a hook angle of about 6° to 20°.

19. The pediatric liver retractor of claim 18, wherein the intermediate portion is substantially arcuate.

20. The pediatric liver retractor of claim 19, wherein the first and second legs are substantially straight.

21. The pediatric liver retractor of claim 19, wherein the arcuate intermediate portion has a radius of about 10 mm to 20 mm.

22. The pediatric liver retractor of claim 18,
wherein the first leg and first end of the intermediate portion are disposed on a first plane, the second leg is oriented at a second angle with respect to the first plane, and the insertion tip is oriented at a downward tip angle with respect to the first plane and at a open tip angle away from the first leg, such that the second leg is angled upwardly towards the liver in the retracted position, and the insertion tip is angled downwardly away from the liver in the retracted position.

23. The pediatric liver retractor of claim 22, wherein the second angle is from about 8° to 13°, the downward tip angle is from about 10° to 30°, and the open tip angle is from about 25° to 45°.

24. The pediatric liver retractor of claim 22, wherein the supporting shaft has a centerline, and the first leg extends from the supporting shaft at a first angle from the supporting shaft centerline measured along the first plane of about 0° to 45°.

* * * * *